United States Patent
Hepler et al.

(10) Patent No.: US 10,145,687 B2
(45) Date of Patent: Dec. 4, 2018

(54) METHOD AND SYSTEM FOR PERSONAL DEAD-RECKONING DRIFT COMPENSATION USING GAIT CHARACTERISTICS

(71) Applicant: Bionic Power Inc., Vancouver (CA)

(72) Inventors: Daniel Loren Hepler, Mission (CA); Clive Edward Mullins, North Vancouver (CA)

(73) Assignee: Bionic Power Inc., Vancouver (CA)

( * ) Notice: Subject to any disclaimer, the term of this patent is extended or adjusted under 35 U.S.C. 154(b) by 265 days.

(21) Appl. No.: 15/224,502

(22) Filed: Jul. 29, 2016

(65) Prior Publication Data
US 2018/0031374 A1 Feb. 1, 2018

(51) Int. Cl.
| | |
|---|---|
| G01C 21/12 | (2006.01) |
| G01C 21/16 | (2006.01) |
| G01C 21/20 | (2006.01) |
| A61B 5/00 | (2006.01) |
| A61B 5/11 | (2006.01) |
| G01C 22/00 | (2006.01) |

(52) U.S. Cl.
CPC .............. *G01C 21/16* (2013.01); *A61B 5/112* (2013.01); *A61B 5/6802* (2013.01); *A61B 5/7207* (2013.01); *G01C 21/165* (2013.01); *G01C 21/20* (2013.01); *G01C 22/006* (2013.01)

(58) Field of Classification Search
CPC ........ G01C 21/16; G01C 21/20; G01C 25/00; G01C 25/005; G01C 21/10–21/18; G01C 22/00–22/006; G01C 21/12

USPC .......... 73/1.01, 1.37, 1.38, 1.41, 1.75, 1.79, 73/1.81, 432.1; 702/33, 85, 90, 94, 95, 702/104, 105, 127, 149, 150, 151, 155, 702/158, 160
See application file for complete search history.

(56) References Cited

U.S. PATENT DOCUMENTS

| | | | |
|---|---|---|---|
| 2008/0077326 A1 | 3/2008 | Funk et al. | |
| 2009/0326795 A1 | 12/2009 | Supino et al. | |
| 2011/0313705 A1* | 12/2011 | Esser | A61B 5/112 702/104 |
| 2013/0311133 A1 | 11/2013 | Kordari et al. | |
| 2014/0156215 A1* | 6/2014 | Eastman | A61B 5/112 702/141 |

OTHER PUBLICATIONS

S. Madgwick, "An efficient orientation filter for inertial and inertial/magnetic sensor arrays". Technical report, Department of Mechanical Engineering, University of Bristol, Apr. 2010.
(Continued)

*Primary Examiner* — Robert R Raevis
(74) *Attorney, Agent, or Firm* — Damien G. Loveland

(57) ABSTRACT

Raw dead reckoning data is obtained from an inertial measurement unit (IMU) worn by a user. Drift in the raw data is compensated for by detecting a gait of the user and phase of that gait, and constraining the position of the IMU to lie within corresponding bounds as the IMU moves. The bounds depend on the bodily geometry of the user and the detected gait phase. The raw orientation data of the IMU may be also corrected for drift in a similar way. Gait and gait phase may be detected by sensors in an energy harvester worn around the knee, for example. Drift in the IMU measurements can be compensated for without depending on a GPS signal or on the earth's magnetic field.

5 Claims, 6 Drawing Sheets

(56) References Cited

OTHER PUBLICATIONS

S. O. H. Madgwick, A. J. L. Harrison and R. Vaidyanathan, "Estimation of IMU and MARG orientation using a gradient descent algorithm," 2011 IEEE International Conference on Rehabilitation Robotics, Zurich, 2011, pp. 1-7.
GPS World Staff, "Continuous Indoor Positioning: GNSS, Wi-Fi, and MEMS Dead Reckoning", (Nov. 1, 2012). Retrieved Jun. 24, 2016, from http://gpsworld.com/continuous-indoor-positioning-gnss-wi-fi-and-mems-dead-reckoning/.
Patent Cooperation Treaty International Search Repot dated Oct. 13, 2017 issued for the co-pending application assigned International Application No. PCT/CA2017/050798 with an International Filing Date of Jun. 30, 2017.
Patent Cooperation Treaty Written Opinion dated Oct. 13, 2017 issued for the co-pending application assigned International Application No. PCT/CA2017/050798 with an International Filing Date of Jun. 30, 2017.

\* cited by examiner

METHOD AND SYSTEM FOR PERSONAL DEAD-RECKONING DRIFT COMPENSATION USING GAIT CHARACTERISTICS

TECHNICAL FIELD

This application relates to a method and system for the compensation of drift in personal dead reckoning. More specifically, this application relates to using the characteristics of a person's gait to compensate for drift in dead-reckoning data that is obtained from a personal inertial measurement unit (IMU).

BACKGROUND

Dead reckoning is the calculation of the current position of a movable object or person based on a previously determined position and a difference in that position using known, estimated or calculated speeds. Dead reckoning is, however, subject to cumulative errors. Gyroscopes have a drift error inherent to them that makes dead reckoning prone to large error accumulation. Gyroscope drift compensation is typically achieved by fusing IMU sensor data with compass heading or global positioning system (GPS) data. FIG. 1 refers to a prior art process for dead reckoning. In step 10, raw positional and orientation measurements are obtained from an accelerometer and gyroscope, based on changes compared to a known reference or given starting point. In step 12, the raw measurements are compensated for drift by taking into account GPS data and/or earth's magnetic field data. The process then outputs the dead reckoned data in step 14.

In an urban setting, however, the earth's magnetic field may be distorted, which may make a drift compensation calculation based on magnetic bearing inaccurate. Also, in urban settings, the GPS signal may be unavailable or be subject to reflections, which prevents a reliable fix from being obtained. Even away from urban settings, GPS signals may sometimes be unavailable or the earth's magnetic field may be subject to local distortions.

Energy may be harvested from the movement of body joints of humans and other animals by converting mechanical energy derived from such movement to electrical energy. Activities where body joints move repeatedly, such as walking, jogging, and running, for example, present opportunities to harvest energy from moving body joints over an extended period of time. FIG. 2 shows a person 20 wearing a prior art energy harvester 22 around his right knee joint. The power produced by a pair of energy harvesters may on average be 10 W, for example.

Energy may be harvested intermittently during a gait cycle, depending on the gait and which phase of a gait the user is in. FIG. 3 includes plots that are representative of various quantities relating to typical dynamics of a knee joint during a walking gait cycle 30. In graph A, plot 32 represents the angular velocity of the knee joint (i.e. the time derivative of the angle of the knee joint), where positive angular velocity represents movement in the knee extension direction and negative angular velocity represents movement in the knee flexion direction. In graph B, plot 33 represents the moment of the knee joint, where a positive moment represents torque in the extension direction and a negative moment represents torque in the flexion direction. Mechanical power associated with movement of the knee joint is the product of the torque (plot 33) and the angular velocity (plot 32) of the knee joint. Harvesting may be controlled by torque profiles that specify how much current to draw from the harvester at each point in the gait cycle. In some cases, an energy harvester may also supply power to the knee joint, to assist the user when tired.

Referring to FIG. 3, gait cycle 30 may generally be divided into a swing portion 36 and a stance portion 37. During the swing portion 36, the foot corresponding to the shaded knee (i.e. the right knee) is off of the ground. In the stance portion 37, the foot corresponding to the shaded knee is on the ground. Swing portion 36 may be further divided into a swing flexion portion 36A, during which the knee is flexing, and a swing extension portion 36B, during which the knee is extending. Stance portion 37 may be further divided into a stance/collision flexion portion 37A, during which the knee is flexing; a stance extension portion 37B, during which the knee is extending; and a swing flexion portion 37C, during which the leg is bending. During one gait cycle 30, angular velocity plot 32 comprises extrema 32A, 32B, 32C and 32D which occur, respectively, in swing flexion portion 36A, swing extension portion 36B, stance/collision flexion portion 37A and stance extension portion 37B. These extrema correspond to the end of acceleration of the knee joint.

Control logic in an energy harvester may include a finite state machine that has multiple states, each of which corresponds to a portion of repetitive motion of a body segment (e.g. a phase or portion of gait cycle 30). Simplified phases that the control logic may use when operating at least in part as a finite state machine are shown in FIG. 4. The states or phases of a complete gait cycle are shown, starting from swing extension 40, during which the subject leg is swinging from a bent position behind the body to a straight position in front of the body. At the end of the swing extension phase 40, i.e. when the heel strikes the ground 42, the collision flexion phase 44 starts. In the collision flexion phase the leg bends slightly at the knee, with the foot on the ground, during which the body's weight is transferred to the subject leg. This is followed by the stance extension phase 46, in which the subject leg straightens out while the foot is still on the ground, propelling the body forward. The following phase is the lowering flexion phase 48, in which the subject leg that is supporting the body's weight bends slightly in order for the other leg to reach forwards more before its heel strikes the ground 50. After the heel of the other leg has struck the ground 50, the swing flexion phase 52 commences, in which the subject leg is lifted from the ground behind the body, continuing the bending motion that started during the lowering flexion phase 48. After the subject leg has finished bending in state 52, the swing extension phase 40 starts again. The torque applied in each phase may either be positive or negative or both, depending on the assistance provided and/or whether energy is harvested. As can be appreciated, a more complex finite state machine, with more narrowly defined states or phases, may be used.

This background information is provided to reveal information believed by the applicant to be of possible relevance to the present invention. No admission is necessarily intended, nor should be construed, that any of the preceding information constitutes prior art against the present invention.

SUMMARY OF INVENTION

The present invention is directed to the use of the characteristics of a person's gait, as sensed by sensors in an energy harvester, to compensate for drift in dead reckoning data obtained from an IMU that is attached to the person.

Starting from a reference point, the bounds of the allowed range of motion of the IMU are determined based on the size and geometry of the user and a detected gait phase. The raw IMU data is then adjusted, if it is outside these bounds, to bring it within the bounds in order to result in dead reckoning data that has been compensated for drift. Drift can be automatically compensated for in the absence of GPS signals and in the presence of unreliable magnetic fields. As a consequence, the resultant dead reckoning data may be improved compared to the fusion of IMU data with unreliable GPS and/or magnetic field data.

Disclosed herein is a method for compensating for drift in dead reckoning calculations for a user undergoing locomotion comprising: attaching an inertial measurement unit (IMU) to the user; defining a first point at which the IMU is located; detecting a phase of a gait of the user using one or more sensors; defining bounds for displacement of the IMU during said phase of the gait; obtaining raw positional data from the IMU for a second point, to which the IMU is displaced by the locomotion of the user; determining whether said raw positional data lies within or outside of said bounds; if the raw positional data lies within the bounds, outputting the raw positional data as dead reckoned data for the second point; and if the raw positional data lies outside the bounds, compensating the raw positional data to result in compensated positional data that is within the bounds and outputting the compensated positional data as the dead reckoned data for the second point.

In some embodiments the method may further comprise: defining a first orientation for the IMU at the first point; defining further bounds for orientation of the IMU during said phase of the gait; obtaining raw orientational data from the IMU for the second point; determining whether said raw orientational data lies within or outside of said further bounds; if the raw orientational data lies within the further bounds, outputting the raw orientational data as dead reckoned data for the second point; and if the raw orientational data lies outside the further bounds, compensating the raw orientational data to result in compensated orientational data that is within the further bounds and outputting the compensated orientational data as the dead reckoned data for the second point.

Further disclosed is a system for compensating for drift in dead reckoning calculations for a user undergoing locomotion comprising: an inertial measurement unit (IMU) attached to the user; and one or more sensors attached to the user. The system is configured to: define a first point at which the IMU is located; detect a phase of a gait of the user using one or more sensors; define bounds for displacement of the IMU during said phase of the gait; obtain raw positional data from the IMU for a second point, to which the IMU is displaced by the locomotion of the user; determine whether said raw positional data lies within or outside of said bounds; if the raw positional data lies within the bounds, output the raw positional data as dead reckoned data for the second point; and if the raw positional data lies outside the bounds, compensate the raw positional data to result in compensated positional data that is within the bounds and output the compensated positional data as the dead reckoned data for the second point.

The system may be further configured to: define a first orientation for the IMU at the first point; define further bounds for orientation of the IMU during said phase of the gait; obtain raw orientational data from the IMU for the second point; determine whether said raw orientational data lies within or outside of said further bounds; if the raw orientational data lies within the further bounds, output the raw orientational data as dead reckoned data for the second point; and if the raw orientational data lies outside the further bounds, compensate the raw orientational data to result in compensated orientational data that is within the further bounds and output the compensated orientational data as the dead reckoned data for the second point.

Still further disclosed is a computer readable medium comprising computer readable instructions, which, when executed by a processor, cause a system for compensating for drift in dead reckoning calculations for a user undergoing locomotion to: define a first point at which an inertial measurement unit (IMU) attached to a user is located; detect a phase of a gait of the user using one or more sensors that are attached to the user; define bounds for displacement of the IMU during said phase of the gait; obtain raw positional data from the IMU for a second point, to which the IMU is displaced by the locomotion of the user; determine whether said raw positional data lies within or outside of said bounds; if the raw positional data lies within the bounds, output the raw positional data as dead reckoned data for the second point; and if the raw positional data lies outside the bounds, compensate the raw positional data to result in compensated positional data that is within the bounds and output the compensated positional data as the dead reckoned data for the second point.

BRIEF DESCRIPTION OF DRAWINGS

The following drawings illustrate embodiments of the invention, which should not be construed as restricting the scope of the invention in any way.

DESCRIPTION

A. Glossary

Figure 1:
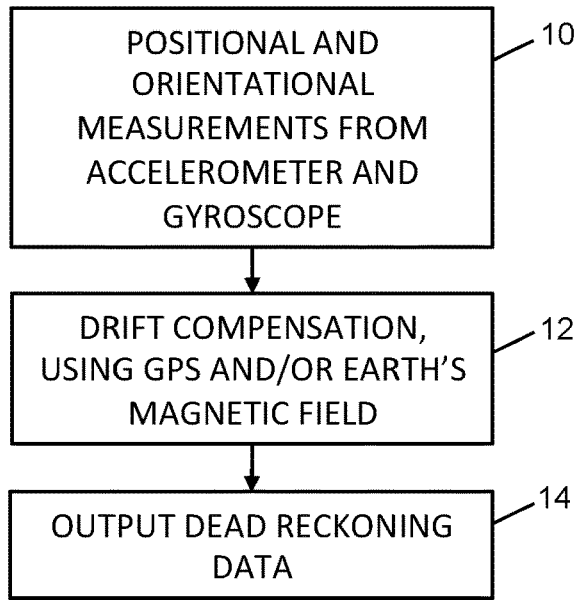
FIG. 1 shows a prior art process for dead reckoning.
Figure 2:
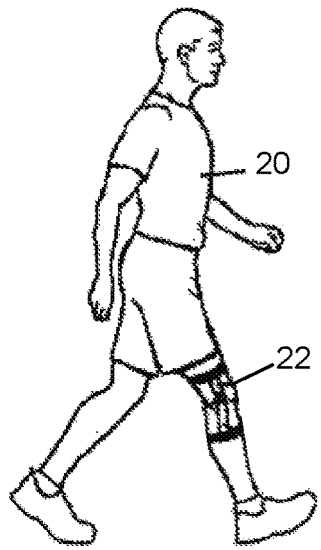
FIG. 2 shows a person wearing a prior art energy harvester.
Figure 3:
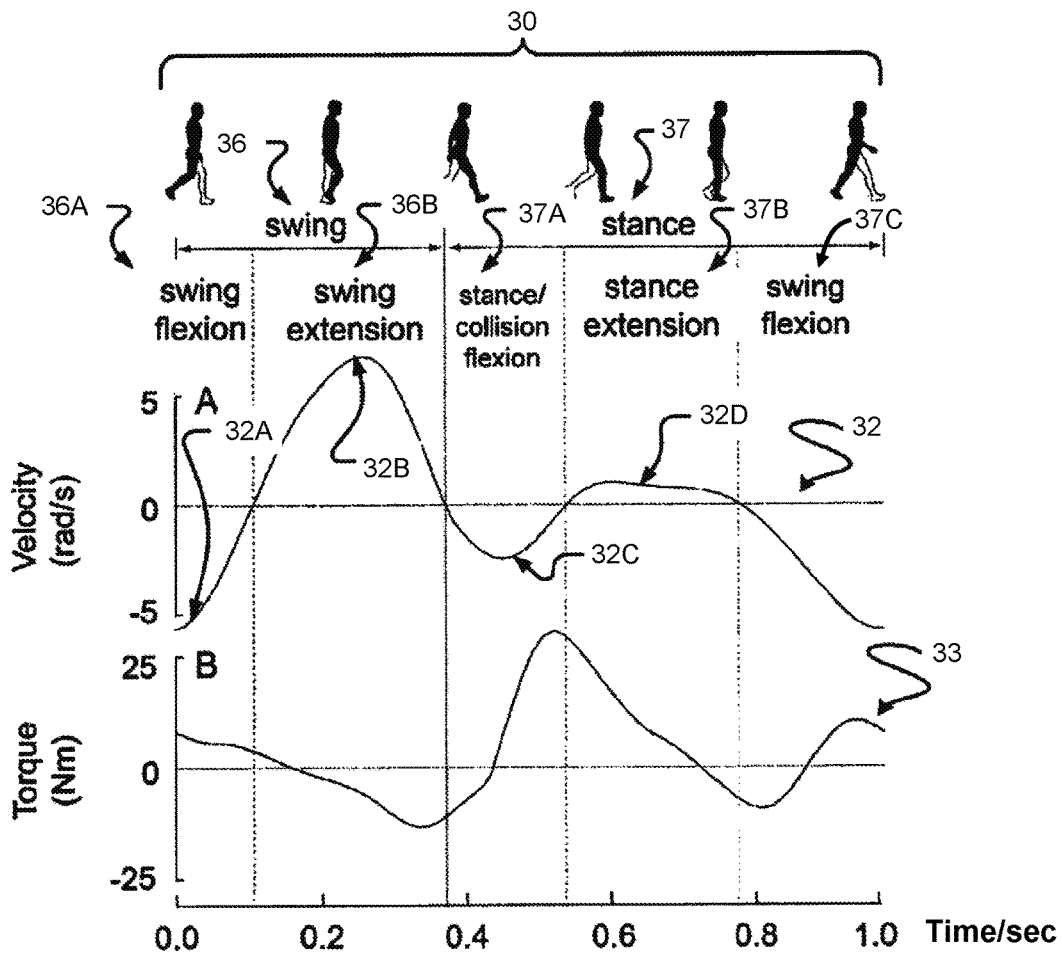
FIG. 3 show prior art plots of angular velocity and torque, which relate to typical dynamics of a knee joint during a walking gait cycle.

The term "dead reckoning" relates to the calculation of the current position of a movable object or person based on a previously determined position, or fix, and a difference in that position using known or estimated speeds or integrated acceleration.

The term "inertial measurement unit (IMU)" refers to a group of one or more sensors that detect the acceleration and/or orientation of a body. It may include one or more accelerometers, such as a triaxial accelerometer for measuring acceleration in three orthogonal directions. It may also include a gyroscope for measuring pitch, yaw and/or roll. Some IMUs may include one or more magnetometers for compensating for drift in measured orientation.

The term "energy harvester" includes any device that converts bio-mechanical motion, such as movement of one or more limbs, to electrical energy, and may include devices in the format of a knee-brace or exo-skeleton, for example. An energy harvester may also be powered, in that it returns kinetic energy to the user of the harvester, for example to assist in walking or to assist in portions of the user's gait.

The term "system" when used herein without qualification refers to a system for detecting gait and providing personal dead reckoning data, including compensating for drift in the dead reckoning calculations using gait phase estimates, the system being a subject of the present invention.

The term "user" refers to a person or animal that is wearing one or more IMUs connected to a dead reckoning drift compensator that employs gait phase estimation. The user may be wearing a bio-mechanical energy harvester that includes the IMUs and drift compensator.

The term "software" includes, but is not limited to, program code that is executed to perform the computations necessary for detecting location, detecting orientation, obtaining sensor readings, detecting gait, detecting gait phase, identifying drift, compensating for drift, storing results and/or other functions.

The term "firmware" includes, but is not limited to, program code and data used to control and manage the sensors, data storage, interfaces and possibly gait models and other functions of the system.

The term "hardware" includes, but is not limited to, the physical housing for a computer, device or system, as well as its display if any, connectors, wiring, circuit boards having processor and memory units, power supply, and other electrical, electronic or mechanical components.

The term "module" can refer to any component in this invention and to any or all of the features of the invention without limitation. A module may be a software, firmware, hardware or mechanical module.

The term "processor" is used to refer to any electronic circuit or group of circuits that perform calculations, and may include, for example, single or multicore processors, multiple processors, an ASIC (Application Specific Integrated Circuit), and dedicated circuits implemented, for example, on a reconfigurable device such as an FPGA (Field Programmable Gate Array). The processor performs one or more of the steps in the flowcharts, whether they are explicitly described as being executed by the processor or whether the execution thereby is implicit due to the steps being described as performed by code or a module. The processor, if comprised of multiple processors, may be located together or separately from each other.

B. Exemplary Embodiments

Figure 5:
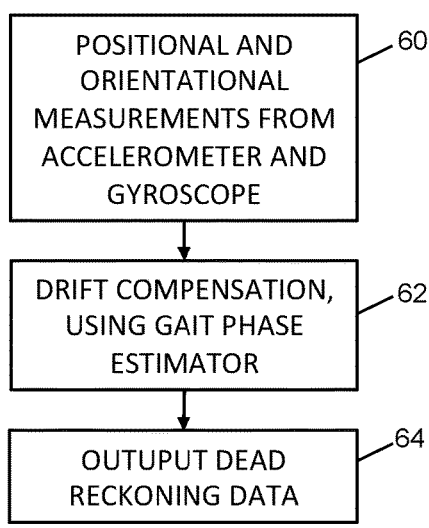
FIG. 5 shows a process for dead reckoning according to an embodiment of the present invention.

Referring to FIG. 5, a flowchart of the main steps of the method for dead reckoning is shown. In step 60, raw positional and orientational measurements are obtained using accelerometers and a gyroscope respectively, by calculating changes from a known or given starting point and known or given orientation. In step 62, any drift that might be present in the obtained raw measurements is detected and compensated for, using a drift compensator. A gait phase estimator determines the most likely phase of gait that the raw measurements were taken over, and the drift compensator adjusts the raw data such that the resulting data lies within bounds that correspond to the detected gait phase. In step 64, the resulting data is output as the dead reckoned data.

Figure 4:
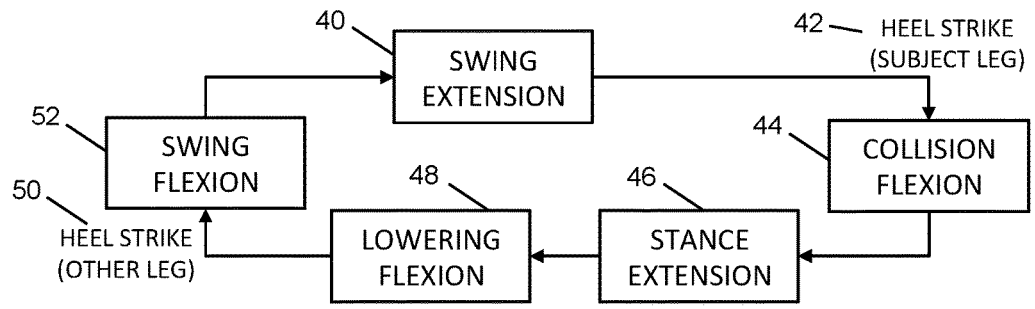
FIG. 4 is a prior art state diagram of various states of a knee joint.
Figure 6:
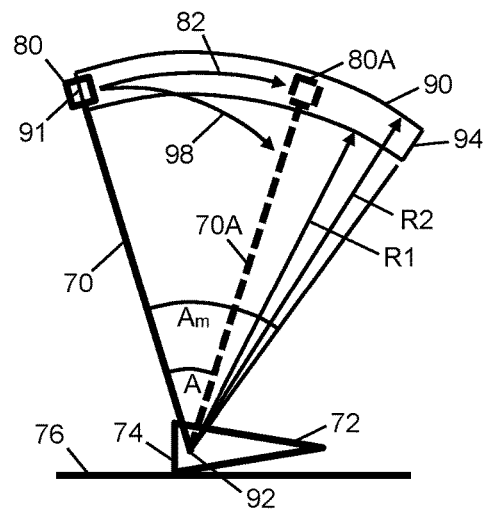
FIG. 6 is a diagram of positional bounds of a sensor attached to lower leg that can pivot at the heel through a maximum angle $A_m$, according to an embodiment of the present invention.

FIG. 6 shows the principle of the method and system for compensating for drift using gait phase estimation, with the various angles exaggerated for clarity. A portion of a lower leg 70 of a user that has just taken a step is shown. The foot 72 is shown with its heel 74 having just made contact with the ground 76. This moment can be categorized as a heel strike event 42 (FIG. 4) in the gait cycle of the user, and it corresponds to the start of the collision flexion phase 44 (FIG. 4) of the gait cycle. The movement of an IMU 80 that is attached to the upper part of the lower leg 70 is shown along arc 82 as the user progresses through the gait cycle to the stance extension phase 46 (FIG. 4).

The IMU 80 is shown to have moved to position 80A, corresponding to the lower leg 70 having moved though an angle A to position 70A. During the whole of this movement, which may be through a combination of two or more constituent phases of the gait, the heel 74 remains in contact with the ground 76 at essentially the same position. As a consequence, the range of motion of the IMU 80 can be deduced to lie within bounds 90. These bounds 90 are formed mainly by arcs of R1 and R2, which are centered at pivot point 92 of the ankle. The bounds 90 connect a start line 91 parallel to and in line with the initial position of the lower leg 70 at the moment of heel strike to an end line 94 defined by the maximum range of motion of the lower leg while the heel 74 is in contact with the ground 76. The end line 94 is defined by angle $A_m$, which is the maximum angle through which the lower leg 70 moves in the gait phase of interest. The angle $A_m$ is provided by a gait phase estimator in the energy harvester, which can detect whether the user is walking on the flat, walking uphill, running or climbing stairs, etc. The bounds 90 have some spatial extent to allow for real world errors in the calculation of the permissible range of motion of the IMU 80 during the gait phase of interest. The start line 91 and end line 94 may be located differently depending on the exact position of the IMU on the lower leg.

Other models may be used to calculate the bounds 90, such as by using a different pivot point (e.g. the back of the heel) or by limiting the bounds to the collision flexion phase 44 of the gait. Different shapes of the bounds 90 are possible. For example, they may not necessarily form a perfect arc, especially if the gait phase used for calculating the bounds includes a portion in which the heel is raised from the ground. In other cases, the bounds may increase in width as the distance from the original position increases, to correspond to an increase in error with distance.

As an example, the IMU 80 may output raw positional data that would indicate that the IMU has moved along path 98 during the portion of the gait phase in which the lower leg 70 moves through angle A. As it can be seen from the diagram, it is not normally possible for the actual position of the IMU to have followed path 98, and it is assumed that the error is caused by IMU drift, from the gyro, the accelerometers or both. The drift in path 98 must therefore be compensated for, by bringing the position as given by the raw data to lie on or inside the bounds 90 as derived from the gait phase. Being on the outer lines or surfaces of the bounds or inside the bounds can both be understood as being within the bounds. If, however, the raw path obtained from the IMU 80 lies within the bounds 90, there is no need to compensate for drift.

Note that in rare cases, the path 98 may be the true path due to the ground suddenly giving way, the energy harvester or IMU falling off, or the user breaking his leg. In these situations, the change or stop in gait will be detected and the system will not use that cycle of the gait to compensate for drift.

The phase of the gait that is used for the drift compensation starts with a heel strike, and ends with either a lift of that heel or a lift of the foot with that heel. Other phases of gait may be used in other embodiments.

Figure 7:
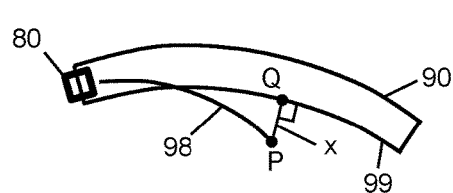
FIG. 7 is a diagram showing a geometrical compensation of drift error according to an embodiment of the present invention.

FIG. 7 shows how the drift in the raw measurements may be compensated for. The point P is the location at the end of path 98, which is given by the raw measurements provided by the IMU 80. One way of compensating for the drift is to minimize the distance from point P to the bounds 90, which occurs when the line joining point P to the bounds is at right angles with the nearest line of the bounds. By doing this, the shortest distance x is found to be between point P and point Q, which is on the lower bound 99. The position output by the system after compensating for drift would therefore be Q rather than P.

There are other ways in which to choose a point on the bounds to represent the compensated dead reckoning location, and such point may be a different point to point Q. For example, the measured orientation of the IMU may be taken into account. By considering only the orientation and compensating for it, a different position on the bounds may result. In some embodiments an average of the two compensated locations could be used as the dead reckoned location. In other embodiments, a weighted average of the two compensated locations could be used that is based on the relative stabilities of the accelerometer and gyroscope.

Figure 8:
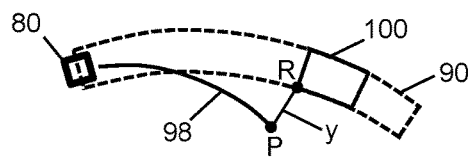
FIG. 8 is a diagram showing a geometrical compensation of drift error according to another embodiment of the present invention.

FIG. 8 shows another way of compensating for drift. Instead of using only bounds 90 to specify the allowed positions of the IMU 80, moving bounds 100 may be used. The motion of the bounds 100 may be dependent on the angle of the knee joint, as provided by an angular sensor installed in the energy harvester. As the angle of the knee changes according to a known or modelled profile as the user progresses through the phase of the gait, the position of the bounds 100 can be changed in response. The progression of the bounds 100 along the envelope of the overall bounds 90 is not necessarily uniform. Alternately, the motion of the bounds 100 may be based on the passage of time, and the bounds may move uniformly or non-uniformly through the envelope of the overall bounds 90.

With moving bounds 100, the drift compensation for position P at the end of path 98, which is given by the raw data obtained from the IMU, may be determined by finding the minimum distance from point P to the bounds 100 at the time that the raw data is obtained. In this case, the shortest line y from point P to the bounds 100 may not be at a right angle to the nearest line of the bounds, as shown by point R, for example. Drift compensation would therefore result in the system outputting point R for the location instead of point P.

Again, the shape of the moving bounds 100 may be different to that shown, and the bounds may change shape and/or size as they move. Also, if the raw path obtained from the IMU 80 lies within the bounds 100, there is no need to compensate for drift.

Figure 9:
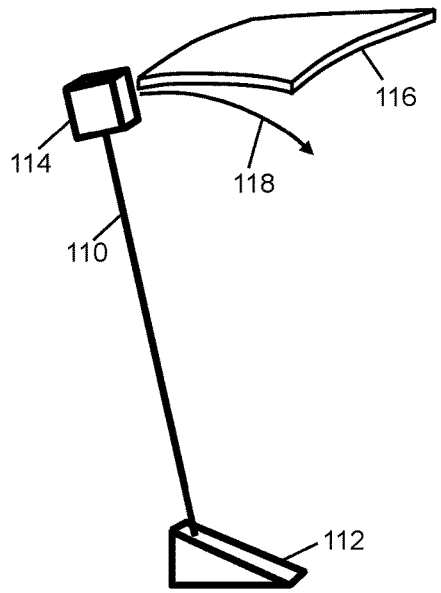
FIG. 9 is a diagram showing three-dimensional positional bounds for a sensor attached to a lower leg, according to an embodiment of the present invention.

FIG. 9 shows a three-dimensional example of a lower leg 110 with foot 112 and IMU 114 attached at the upper region of the lower leg. The heel of the foot 112 has just struck the ground and the user has just entered the collision flexion phase of the gait. The bounds 116 are shown in the form of a complex curved mat. The path 118 of the IMU as given by the raw data from the IMU can be corrected so that any point of it lies on the surface of the bounds 116 at a minimized distance from that point to the bounds. The bounds can have some width to the left and right of the user to allow for turning as the user walks. In another embodiment, smaller, moving three-dimensional bounds may be used. If the raw path obtained from the IMU 80 lies within the bounds 116, there is of course no need to compensate for drift.

In a similar fashion, the orientation given by the raw data produced by the gyroscope in the IMU 80 may be bounded to lie within limits that are dependent on the specific phase of the gait of the user. Calculations to compensate for drift in the raw orientation data may be performed by correcting the orientation, if outside the bounds, to be equal to the nearest value of the bounds. In one plane, for example the horizontal plane in which a yaw drift may occur, the bounds would be two numbers specifying maximum and minimum heading angles, between which the permissible orientation would lie. Roll angle can be corrected for in a similar way by constraining the measured angle of dip to lie between two values. If compensating for drift in both yaw and pitch, a cone may be used to represent bounds for the permissible angles. The measured orientation, if outside the cone, would be corrected to lie on the nearest surface of the cone. Shapes other than a cone may be used, such as an elliptical cone or an irregular shape.

There are many ways to perform a drift compensation calculation. Iterative approaches and least squares methods may be used, for example. In some embodiments, Kalman filtering or a variant thereof may be used to determine the position of the user from the raw data and the prediction from the gait phase estimation and bounds calculation. Other methods that determine a quantity based on a measurement and a prediction may also be used.

Figure 10:
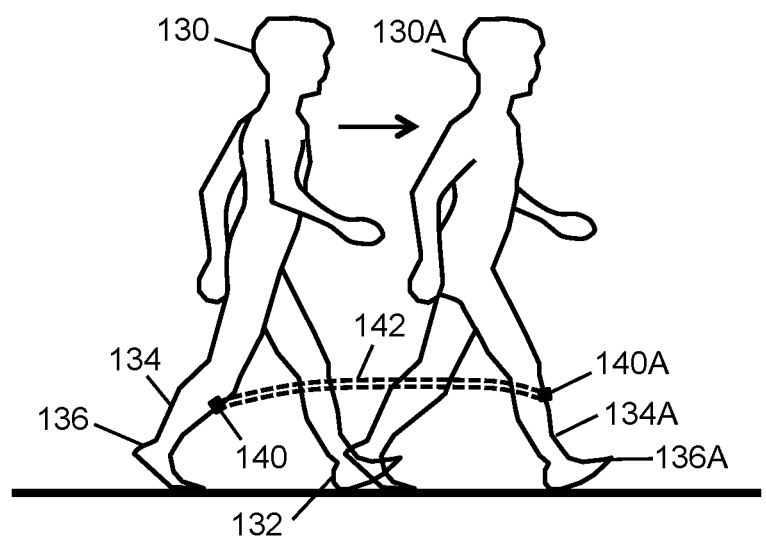
FIG. 10 is a diagram of positional bounds of a sensor attached to lower leg that swings while the other foot is on the ground, according to an embodiment of the present invention.

Referring to FIG. 10, a person 130 is shown taking a step in the direction of the arrow to position 130A. In the initial position, the left heel 132 of the person 130 has just struck the ground and so the left leg has just entered the collision flexion phase of the gait. During the step, the right lower leg 134 and right heel 136 move to positions 134A and 136A respectively. An IMU 140 that is mounted on the right lower leg 134 moves within bounds 142 to position 140A as the step is taken. The bounds 142 are calculated based on the position of the IMU 140 on the right lower leg 134 relative to the ground and/or the pivot point of the right ankle, and/or the height of the right ankle joint above the ground, allowing for footwear worn by the user. The bounds 142 are also calculated based on the lengths of the lower legs and upper legs from the centers of their pivot points, and optionally the distance between the user's hip joints. The calculation of the bounds 142 can be further refined by taking more parameters into consideration, such as the extent to which a user's hips twist during the phase of gait, or the fact that the knee joint is a sliding and pivoting joint. In general, the bounds are defined based on one or more dimensions of the user, and one or more ranges of motion of one or more body parts of the user.

In other embodiments, a simple approximation may be made to constrain the position of the IMU 140 to within a fixed distance of another IMU on the user's other lower leg, or even on another part of the user's body.

Figure 11:
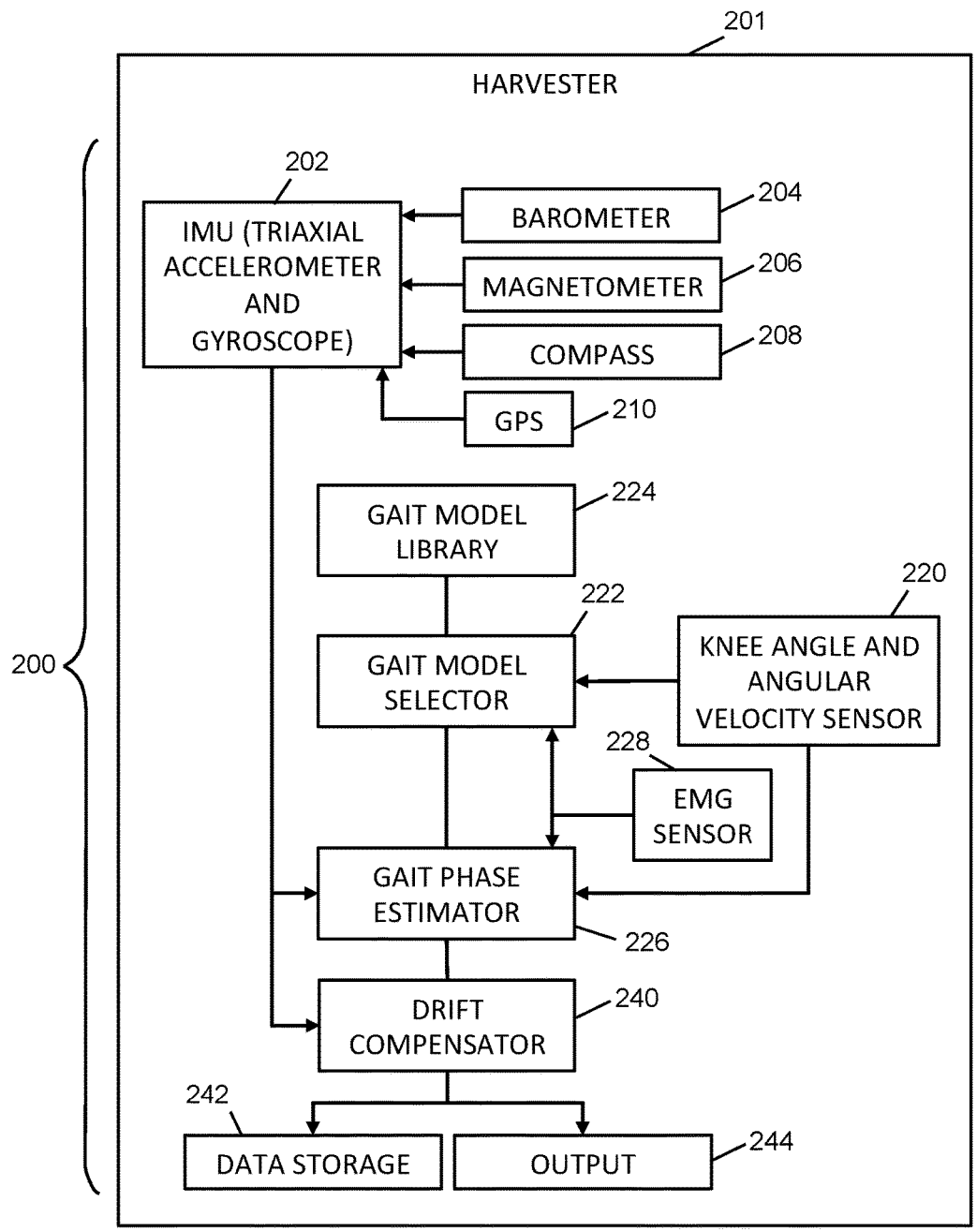
FIG. 11 is a graphical representation of a system for dead reckoning, in accordance with an embodiment of the present invention.

FIG. 11 shows a block diagram of the various modules in the system 200 for compensating drift in IMU measurements. The system 200 is included as part of an energy harvester 201. The modules of the system 200 represent program code that is executed by one or more processors in the harvester 201. Code may be stored as computer readable instructions in a computer readable medium in the system 200.

An IMU 202, which includes a triaxial accelerometer and a gyroscope, provides raw positional and orientation data. There are many IMUs available on the market. Depending on the IMU, processing of the detected data may be performed within the IMU, or by a processor external to it, to result in uncompensated location and orientation data. Optionally, the IMU may take inputs from a barometer 204 for measuring atmospheric pressure and determining elevation above sea level, a magnetometer 206 for measuring the earth's magnetic field, and a compass 208 for determining heading. Depending on the particular IMU 202 used, the barometer 204, magnetometer 206 and compass 208 may be external from or internal to the IMU. Also, a GPS device 210 may optionally be included, either separate from the IMU 202 or internal to it. These additional sensors 204-210 may or may not be used, and even if they are used, increased accuracy may be obtained by further compensating for the drift using gait phase estimation.

Other sensors in the energy harvester 201 include a knee angle sensor (i.e. goniometer) and/or a knee angular velocity sensor 220. These particular sensors are part of the energy harvester 201, and are used for determining gait phases for the purpose of controlling the intermittent harvesting of energy in order to optimize it. Harvesting of energy is controlled by controlling the current drawn by a generator, which in turn controls the torque applied to the joint. By optimizing the pattern of torque applied to the joint, the impact of energy harvesting on the user can be minimized. The knee angle and/or angular velocity sensors 220 provide outputs to the gait model selector module 222, which selects the most appropriate gait model from a library of gait models 224. The gait model selector 222 extracts features of the patterns of data provided to it from the sensors 220, compares these features to features in the gait models in the gait model library 224, and selects the closest match. The models of gait in the gait model library 224 are programmed in. In other embodiments, there may be a learning module that learns the user's different gaits and automatically creates models for them.

The knee angle and angular velocity sensors 220 also provide output data to the gait phase estimator 226. The gait phase estimator 226 looks for features in the patterns of data provided by the sensors 220 and compares them to features in the selected gait model. When there is a match, the gait phase estimator can then output the phase of the gait that the user is in. The gait phase estimator may also take as an input the raw data from the IMU 202. The gait phase estimator is referred to as an estimator because of the difficulty, sometimes, in identifying the exact start and finish of a particular phase of a gait, and because there are usually natural variations in a user's gait or in the terrain that is traversed.

There may be an EMG sensor 228 in the harvester 201, which detects muscle activity. Outputs from the EMG sensor 228 may be fed to the gait selector module 222 and/or the gait phase estimator 226 in order to provide additional information to assist with the gait model selection and gait phase estimation processes respectively.

The output of the gait phase estimator 226 is passed to the drift compensator module 240, which also takes as input the raw data from the IMU 202. The drift compensator determines whether the raw data lies within the bounds corresponding to the estimated gait phase, and if it doesn't, it corrects the raw data such that it lies within the bounds. If the raw data lies within the bounds, the drift compensator 240 does not need to correct it. While the barometer 204, magnetometer 206, compass 208 and GPS device 210 have been shown to provide input to the IMU 202, they may instead provide input to the drift compensator 240.

The drift compensator 240 is connected to a data storage module 242, which stores the dead reckoned positional and orientation data that is provided by the drift compensator. The drift compensator 240 is also connected to an output 244, which transmits the dead reckoned data to a remote monitoring computer.

While drift compensation for the position and orientation has been discussed above in relation to the IMU, it is to be understood that at any moment the position and orientation of the user can be deduced from the position and orientation of the IMU, taking into account where the user is in the gait cycle. This function may be part of the drift compensator 240, for example, or it may be in a separate module.

Figure 12:
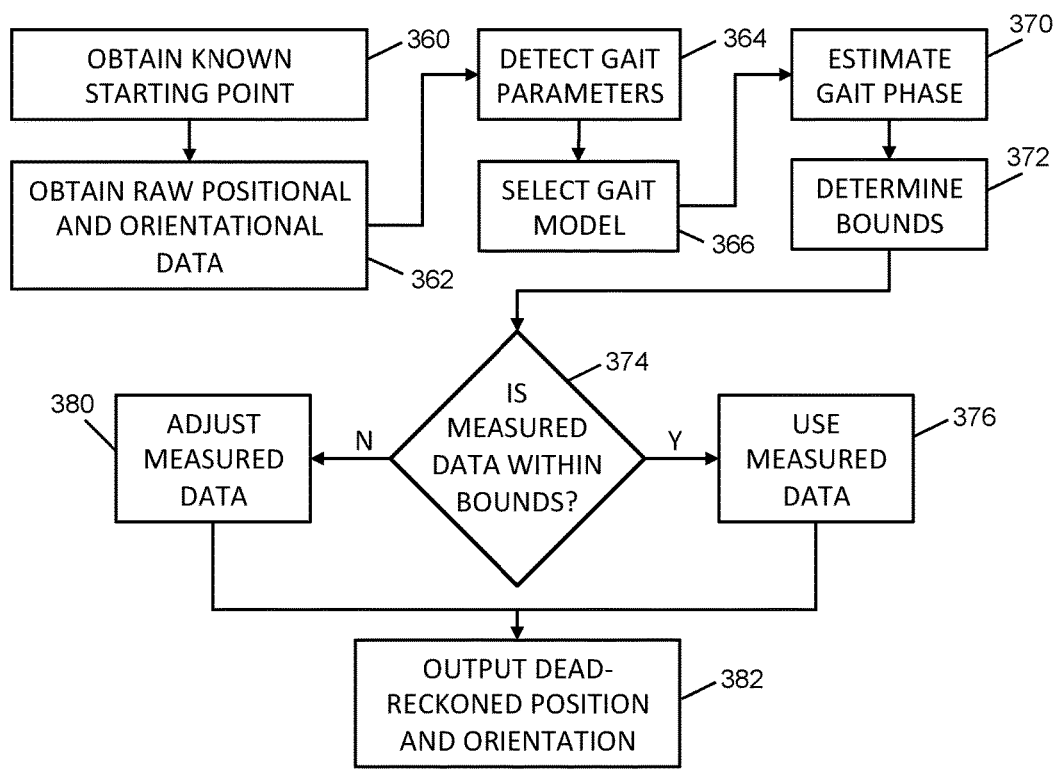
FIG. 12 is a flowchart of a process for dead reckoning carried out by the present invention.

A more detailed method performed by a system 200 for compensating for drift in dead reckoning calculations is shown in the flowchart of FIG. 12. In step 360, a known starting point is obtained by the drift compensator 240. This may be, for example, a reliable GPS location (e.g. from module 210), a longitude and latitude, a landmark, etc. It may also be a dead reckoned location as calculated from a previous cycle of the method, and retrieved, for example, from the data storage module 242. The known starting point also includes a heading of the IMU 202 or user, which may be obtained from a reliable compass 208 or from a previous cycle of the method.

In step 362, measurements of acceleration are obtained from the IMU 202 and, knowing the velocity of the IMU at the starting point and the location of the starting point, the position of the IMU at a later point in time is calculated by integrating the acceleration twice. The integration may be done within the IMU 202 or in the drift compensator module 240. This calculation of the location is the raw positional data obtained from the IMU 202. The raw orientational data is also obtained from the IMU 202, from its gyroscope.

In step 364, the gait model selector 222 and gait phase estimator 226 detect the parameters of the user's gait. The input to the gait model selector 222 and gait phase estimator 226 may be the angular velocity and angle of the knee, from module 220, along with a model-based algorithm from library module 224, or it may include input from IMU-based or electromyography (EMG)-based gait phase estimators, such as EMG sensor 228. Any type of sensor may be used in various different embodiments for providing input to the gait model selector 222 and the gait phase estimator 226.

In step 366, the gait model selector module 222 selects the most appropriate gait model from a selection of available models in the library 224. Each type of human locomotion, such as walking, jogging, running, sprinting, climbing stairs, descending stairs, ascending an incline, descending an incline, scrambling, side-stepping, jumping, etc. has a different gait model. The selection of the gait model is made by matching the detected gait parameters obtained in step 364 with the features of the available gait models.

In step 370, after the gait model has been selected, the gait phase estimator 226 estimates which phase of the selected gait the user is in. The estimation of the gait phase is achieved by matching the detected gait parameters obtained in step 364 with the features of the selected gait model.

In step 372, the gait phase estimator 226 calculates or retrieves the bounds that correspond to the estimated phase of the selected gait. The bounds or the formula for their calculation may be stored in a database accessible by the gait phase estimator, for example in the gait model library 224.

In step 374, the raw data provided by the IMU 202 is tested by the drift compensator 240 to determine whether it lies within the bounds or not. If the raw data lies within the bounds, then it can be assumed that there is no drift, or that any drift that may be present in the data is within an allowable tolerance as specified by the bounds. Step 376 follows from the decision point in step 374 if the raw data lies within the bounds. In step 376, the raw (i.e. uncompensated) data from the IMU 202 is used as the dead reckoned location and orientation.

Step 380 is taken if the raw, measured data lies outside the bounds. In this case, it is assumed that there has been some drift in the data provided by the IMU. In step 380, the raw, measured data is adjusted by the drift compensator 240 to compensate for the drift, by bringing the measured values back to the nearest point on the bounds. The compensation results in a dead reckoned location and orientation that is more reliable than if the compensation had not been applied to the raw data. The compensation in the dead reckoned data is also more accurate than magnetic field compensation based on a poor magnetic field or on poor GPS signals.

In step 382, the resulting dead reckoned data, whether obtained with or without compensation, is output from the drift compensator. The output may be to a memory device 242 in the energy harvester in which the drift compensator is located, or it may be transmitted wirelessly to a monitoring computer by output module 244. Prior to storage and/or transmission, or after storage, the dead reckoned data for the IMU 202 may be converted to dead reckoned data for the user.

C. Variations

While the best presently contemplated mode of carrying out the subject matter is disclosed and claimed herein, it will be clear to one having skill in the art that variations to the specific details disclosed herein can be made, resulting in other embodiments that are within the scope of the invention disclosed.

Modules of the system may be divided into constituent modules or they may be duplicated. The division of functions between the various modules of the system may be changed without altering the overall functions of the system. Arrows between the modules of the system may be other than shown, and may be one way or two way in other embodiments. Steps in the flowcharts may be amended, repeated, omitted or performed in a different order while remaining within the scope of the invention. All parameters, dimensions, relative dimensions, angles, shapes and configurations described herein are examples only and actual values of such depend on the specific embodiment. In general, unless otherwise indicated, singular elements may be in the plural and vice versa with no loss of generality. Use of the masculine is intended to include the feminine.

The lower down on the user's lower leg that the IMU is placed, the smaller the volume of the bounds will be and the more accurate the compensated dead reckoning will be. This applies to the case where the phase of gait that is used is that when the heel of the leg with the IMU is in contact with the ground. It also applies when the heel is lifted but the front part of the foot is still on the ground. However, the range of the dead reckoned displacement is correspondingly less.

Different phases of the gait may be used, as well as gait events such as heel strike and toe-off. Partial phases of the gait may be used or multiple gait phases may be combined for use, either in full or in part. Different moments of the gait phase may be selected as the starting point in the calculation for the compensation of drift.

Multiple dead reckoned measurements may be made consecutively and compensated for, to allow for continuous tracking of the user's position and orientation. In this case, each gait phase used for the calculation should start at the moment the immediately preceding gait phase ends, or there may be an overlap in gait phases that are used.

Gait phases where both a person's feet are in the air, for example when running, may also be used. The bounds in this case may then depend on the estimated speed of the user when off the ground.

The shape of the bounds 90, 100, 116, 142 may be different. For example, they may be irregular, pie-shaped, complex or linear. Determination as to whether the raw data lies within or outside of the bounds may be performed by taking into consideration a tolerance value.

Two IMUs may be used, one for each leg of a user. The bounds of each can be further limited by not allowing the locations of each to separate from each other by more than a fixed amount that depends on the shape and size of the user, and the locations of the IMUs on the user. The use of two IMU's would be of particular benefit over greater distances than one or a few strides.

The IMU can be located on any part of the user's body and can be constrained to move within bounds that are calculated based on the user's gait and body geometry. For example, the IMU sensor may be placed only on the upper leg, and a goniometer may be used to estimate the motion of the lower leg.

The invention may also be applied to users who are cycling, with the bounds determined by the user's body geometry and the geometry of the bicycle. The invention may also be applied to cross-country skiing. Other uses are also contemplated, including the use by amputees or people with paraplegia. The invention may also be applied to animals.

Even though the invention has been described in relation to a drift compensator that forms part of an energy harvester, the drift compensator may be used irrespectively of whether the energy harvester is generating electricity or not, or whether it is providing assistive power to the joint. The drift compensator may also be used outside of an energy harvester, provided that the necessary components are included in the system for its proper functioning.

Throughout the description, specific details have been set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

The detailed description has been presented partly in terms of methods or processes, and symbolic representations of operations, functionalities and features of the invention. These method descriptions and representations are the means used by those skilled in the art to most effectively convey the substance of their work to others skilled in the art. A software implemented method or process is here, and generally, understood to be a self-consistent sequence of steps leading to a desired result. These steps require physical manipulations of physical quantities. Often, but not necessarily, these quantities take the form of electrical or magnetic signals or values capable of being stored, transferred, combined, compared, and otherwise manipulated. It will be further appreciated that the lines between hardware, firmware and software are not always sharp, it being understood by those skilled in the art that the software implemented processes described herein may be embodied in hardware, firmware, software, or any combination thereof. Such processes may be controlled by coded instructions such as microcode and/or by stored programming instructions in one or more tangible or non-transient media readable by a computer or processor. The code modules may be stored in any computer storage system or device, such as hard disk drives, optical drives, solid-state memories, etc. The methods may alternatively be embodied partly or wholly in specialized computer hardware, such as ASIC or FPGA circuitry.

Accordingly, the scope of the invention is to be construed in accordance with the substance defined by the following claims.

The invention claimed is:

1. A system for compensating for drift in dead reckoning calculations for a user undergoing locomotion comprising:
   an inertial measurement unit (IMU) attached to the user;
   one or more sensors attached to the user;
   one or more processors; and
   modules of program code;
   wherein the modules of program code are configured, when executed by the one or more processors, to:
     define a first point at which the IMU is located;
     detect a phase of a gait of the user using the one or more sensors;
     define bounds for displacement of the IMU during said phase of the gait;
     obtain raw positional data from the IMU for a second point, to which the IMU is displaced by the locomotion of the user;
     determine whether said raw positional data lies within or outside of said bounds;
     if the raw positional data lies within the bounds, output the raw positional data as dead reckoned data for the second point; and
     if the raw positional data lies outside the bounds, compensate the raw positional data to result in compensated positional data that is within the bounds and output the compensated positional data as the dead reckoned data for the second point.

2. The system of claim 1, wherein said one or more sensors include one or both of a knee angle sensor and a knee angular velocity sensor.

3. The system of claim 1, wherein said modules of program code are further configured, when executed by the one or more processors, to:
   define a first orientation for the IMU at the first point;
   define further bounds for orientation of the IMU during said phase of the gait;
   obtain raw orientational data from the IMU for the second point;
   determine whether said raw orientational data lies within or outside of said further bounds;
   if the raw orientational data lies within the further bounds, output the raw orientational data as further dead reckoned data for the second point; and
   if the raw orientational data lies outside the further bounds, compensate the raw orientational data to result in compensated orientational data that is within the further bounds and output the compensated orientational data as the further dead reckoned data for the second point.

4. The system of claim 1 wherein said IMU, one or more sensors, modules of program code and one or more processors are embodied within an energy harvester.

5. A tangible computer readable medium comprising computer readable instructions, which, when executed by a processor, cause a system for compensating for drift in dead reckoning calculations for a user undergoing locomotion to:
   define a first point at which an inertial measurement unit (IMU) attached to a user is located;
   detect a phase of a gait of the user using one or more sensors that are attached to the user;
   define bounds for displacement of the IMU during said phase of the gait;
   obtain raw positional data from the IMU for a second point, to which the IMU is displaced by the locomotion of the user;
   determine whether said raw positional data lies within or outside of said bounds;
   if the raw positional data lies within the bounds, output the raw positional data as dead reckoned data for the second point; and
   if the raw positional data lies outside the bounds, compensate the raw positional data to result in compensated positional data that is within the bounds and output the compensated positional data as the dead reckoned data for the second point.

* * * * *